United States Patent
Zheng et al.

(10) Patent No.: US 10,450,243 B2
(45) Date of Patent: Oct. 22, 2019

(54) SULFIDING PROCESS FOR AROMATIC TRANSALKYLATIONS

(71) Applicant: ExxonMobil Chemical Patents Inc., Baytown, TX (US)

(72) Inventors: Xiaobo Zheng, Houston, TX (US); Robert G. Tinger, Friendswood, TX (US); Timothy P. Bender, Houston, TX (US); Kathleen M. Keville, Beaumont, TX (US); Jeffrey L. Andrews, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 17 days.

(21) Appl. No.: 14/861,707

(22) Filed: Sep. 22, 2015

(65) Prior Publication Data

US 2016/0176786 A1     Jun. 23, 2016

Related U.S. Application Data

(60) Provisional application No. 62/094,177, filed on Dec. 19, 2014.

(51) Int. Cl.
*C07C 6/06* (2006.01)
*B01J 37/20* (2006.01)
(Continued)

(52) U.S. Cl.
CPC .............. *C07C 6/06* (2013.01); *B01J 29/06* (2013.01); *B01J 35/0006* (2013.01); *B01J 37/20* (2013.01); *C07C 6/126* (2013.01); *B01J 29/48* (2013.01); *B01J 29/7469* (2013.01); *B01J 29/80* (2013.01); *C07C 2529/48* (2013.01); *C07C 2529/74* (2013.01); *C07C 2529/80* (2013.01); *Y02P 20/52* (2015.11)

(58) Field of Classification Search
CPC ........................................................ B01J 37/20
See application file for complete search history.

(56) References Cited

U.S. PATENT DOCUMENTS 5,030,787 A     7/1991   Absil et al.
5,763,720 A *   6/1998   Buchanan ............ B01J 29/7415
                                                                  585/475

(Continued)

FOREIGN PATENT DOCUMENTS

WO    WO2012/074613    6/2012
WO    WO2012/173755    12/2012
WO    WO2014/193563    12/2014

*Primary Examiner* — Philip Y Louie
*Assistant Examiner* — Alyssa L Cepluch

(57) ABSTRACT

A process is provided for producing xylene by transalkylation including introducing sulfur into a reactor containing a catalyst system prior to first introduction of hydrocarbon feedstock into the reactor; introducing hydrocarbon feedstock into the reactor upon the concentration of sulfur downstream of the catalyst system meeting a predetermined sulfur breakthrough concentration; continuing sulfur introduction for a period of time after first introducing hydrocarbon feedstock into the reactor; reducing the concentration of sulfur introduced upon ΔT decreasing to or below a predetermined sulfur reduction threshold; and discontinuing sulfur introduction upon ΔT decreasing to or below a predetermined sulfur shutoff threshold.

25 Claims, 1 Drawing Sheet

(51) Int. Cl.
*B01J 35/00* (2006.01)
*B01J 29/06* (2006.01)
*C07C 6/12* (2006.01)
B01J 29/48 (2006.01)
B01J 29/74 (2006.01)
B01J 29/80 (2006.01)

(56) References Cited

U.S. PATENT DOCUMENTS

| | | |
|---|---|---|
| 5,942,651 A | 8/1999 | Beech, Jr. et al. |
| 6,893,624 B2 | 5/2005 | Lai et al. |
| 7,148,391 B1 | 12/2006 | Buchanan et al. |
| 7,439,204 B2 | 10/2008 | McMinn et al. |
| 7,553,791 B2 | 6/2009 | McMinn et al. |
| 7,663,010 B2 | 2/2010 | Levin |
| 7,692,052 B2 * | 4/2010 | Frey .................. C07C 6/126 208/133 |
| 8,071,828 B2 | 12/2011 | Cao et al. |
| 8,163,966 B2 | 4/2012 | Levin |
| 8,183,424 B2 | 5/2012 | Levin et al. |
| 8,242,322 B2 | 8/2012 | Boldingh |
| 8,586,809 B2 | 11/2013 | Beech, Jr. et al. |
| 8,822,363 B2 | 9/2014 | Levin et al. |
| 2012/0065446 A1 * | 3/2012 | Boldingh .................. B01J 29/80 585/481 |
| 2012/0083635 A1 | 4/2012 | Boldingh et al. |
| 2012/0083636 A1 * | 4/2012 | Boldingh .................. B01J 29/80 585/401 |
| 2013/0267748 A1 | 10/2013 | Beech, Jr. et al. |
| 2015/0025283 A1 | 1/2015 | Cheng et al. |

* cited by examiner

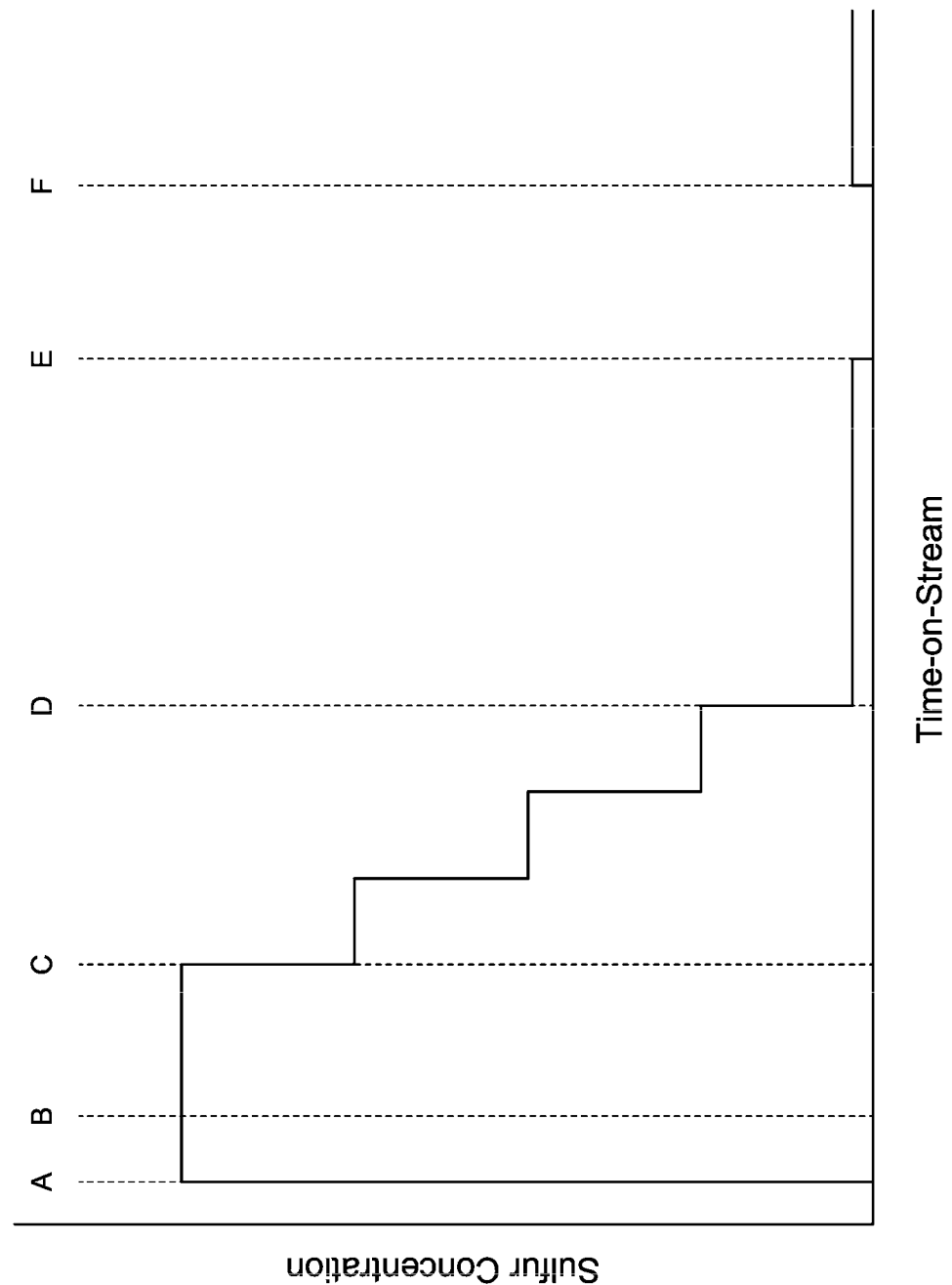

SULFIDING PROCESS FOR AROMATIC TRANSALKYLATIONS

CROSS REFERENCE TO RELATED APPLICATIONS

This application claims priority to and the benefit of U.S. Provisional Application No. 62/094,177, filed Dec. 19, 2014 which is incorporated herein by reference in its entirety. This application is related to concurrently filed U.S. patent application Ser. No. 14/861,783 (U.S. Provisional Application No. 62/073,625).

FIELD OF THE INVENTION

The invention relates to a process for producing xylenes including the sulfiding of one or more catalysts.

BACKGROUND OF THE INVENTION

The demand for xylenes, particularly paraxylene, has increased in proportion to the increase in demand for polyester fibers and film. Processes for producing xylenes include transalkylation, disproportionation, toluene alkylation with methanol, among others, certain of which are capable of producing paraxylene selectively, i.e., in amounts greater than thermodynamic equilibrium (23 mol % based on the xylene isomers at typical processing conditions). Another important reaction in making paraxylene is the well-known xylenes loop, which involves the extraction of paraxylene, typically by adsorption or crystallization, leaving behind a paraxylene-depleted stream ("raffinate"), which is isomerized by liquid or vapor phase isomerization, or a combination thereof, to an equilibrium mixture of xylenes, followed by recycle to the paraxylene extraction step. All of these and other processes may be integrated in various ways, generally with the goal of optimizing paraxylene production economically. Virtually all of these processes, as well as many processes involved with the production of chemicals other than xylenes, utilize catalysts which benefit in some way by having their activity attenuated, at some point in the process, by sulfiding, coking, silicon-selectivation, and the like.

For instance, the manufacture of xylene using transalkylation processes may utilize one or more catalysts to convert feed streams containing benzene and/or toluene (collectively, $C_{7-}$ aromatic hydrocarbons) and feed streams containing heavy aromatics, i.e., $C_{9+}$ aromatic hydrocarbons, into a xylene-containing product stream. See, for instance, U.S. Pat. Nos. 5,030,787; 5,763,720; 5,942,651; 6,893,624; 7,148,391; 7,439,204; 7,553,791; 7,663,010; 8,071,828; 8,163,966; 8,183,424; 8,586,809; and 8,822,363; Publication Nos.; 2013-0267748; 2015-0025283; WO2012/074613; WO2014/193563 and WO2012/173755.

A typical transalkylation process may comprise contacting the combined $C_{7-}$ aromatic hydrocarbon stream with the $C_{9+}$ aromatic hydrocarbon stream with a first catalyst comprising a zeolite (e.g., ZSM-12, ZSM-11, and the like) and a hydrogenation component, such as a platinum-group metal, to provide for dealkylation/transalkylation, to produce a first product, and then contact of the first product with a second catalyst (e.g., ZSM-5), without a hydrogenation component, to crack certain undesired co-boilers, including those produced in the dealkylation process. Co-boilers are those species which boil at or near the boiling point of one of the desired aromatic products, making separation by fractionation difficult.

One of the key undesirable side reactions in such a transalkylation process, or any of the aromatics processes using a catalyst having a hydrogenation component, is ring saturation of the aromatic moiety, e.g., the aromatic ring is saturated to a naphthene, and the naphthene is then subsequently hydrocracked to lighter paraffins, namely $C_2$ and $C_3$ species. This has two impacts—it downgrades aromatics to fuel gas—and it may result in a higher amount of co-boilers.

On fresh start-up (the first time the catalyst contacts hydrocarbon feed) the hydrogenation metal, such as platinum, will ring saturate and crack at very high levels. This reaction is exothermic, and the exotherm can actually exceed the design temperatures of the equipment. Because of this, there is a need to temper the metal activity. One way to do this is to passivate the metal, i.e., lower the activity, to allow for start-up. One method of passivation is to use sulfur which, without wishing to be bound by theory, sorbs onto the hydrogenation metal and decreases its ability to cause ring saturation. For reactions such as transalkylation, passivation may include pre-sulfiding (before feed introduction) and/or co-sulfiding (meaning the sulfur is introduced with the hydrocarbon feed) the catalyst.

Sulfiding a supported metal catalyst by pre-sulfiding or co-sulfiding is a well-known technique but with several known negative effects, which include: (1) sulfur in the feed can result in sulfur in the product and/or potential sulfur poisoning of processes downstream; and (2) sulfur may cause permanent deactivation of some active sites, affecting the useful life of the catalyst. Thus, sulfiding is usually limited to pre-sulfiding or co-sulfiding for some short period of time during catalyst start-up.

In an example of a known process, U.S. Pat. No. 5,763,720 proposes pre-sulfiding a zeolite transalkylation catalyst system and subsequently co-sulfiding with introduction of a hydrocarbon feed stream at a sulfur concentration of 50 to 10,000 ppmw for up to 10 days. Additionally, U.S. Pat. No. 8,242,322 proposes intermittently introducing sulfur to a transalkylation catalyst after 2 days on stream in small quantities, i.e., 1-150 ppm by weight, in order to improve benzene purity in addition to or alternatively to in situ sulfiding within the first 2 days on stream.

After initial sulfiding, the catalyst can still be over-active. Because of this, the reactor is typically run at sub-optimal conditions during a "line-out" or "de-edging" period. For example, during de-edging, the reactor may be run with a partial pressure of hydrogen substantially less than designed in order to lessen ring saturation and cracking and controllably coke the hydrogenation metal of the catalyst. This de-edging period may typically last from several weeks to several months for transalkylation.

It has surprisingly been discovered that the de-edging period for transalkylation can be accelerated, i.e., optimal reaction conditions can be reached quicker, with no substantial deleterious effects on catalyst performance by pre-sulfiding/co-sulfiding according to a profile tailored to the exotherm of the transalkylation reaction.

SUMMARY OF THE INVENTION

The invention is directed to a process for producing xylene by transalkylation including introducing sulfur to the reaction zone according to a profile tailored to the exotherm of the transalkylation reaction for the purpose of reaching optimal reaction times quicker after catalyst start-up.

A process for producing xylene by transalkylation of two or more hydrocarbon feedstocks may include introducing sulfur into a reactor containing a catalyst system prior to first introduction of hydrocarbon feedstock into the reactor; introducing hydrocarbon feedstock into the reactor upon the concentration of sulfur downstream of the catalyst system meeting a predetermined sulfur breakthrough concentration, which may range between 1-200 ppm by volume; and continuing sulfur introduction for 1-24 hours after first introducing hydrocarbon feedstock into the reactor.

The process may also include reducing the concentration of sulfur introduced upon $\Delta T$ decreasing to or below a predetermined sulfur reduction threshold, which may range between 25° C. and 75° C., wherein $\Delta T$ is the difference between a temperature in the reactor upstream of the catalyst system and a temperature in the reactor downstream of the catalyst system, and may also include discontinuing sulfur introduction upon $\Delta T$ decreasing to or below a predetermined sulfur shutoff threshold, which may range between 5° C. and 25° C. and may be less than the predetermined sulfur reduction threshold.

The process may also include reducing the concentration of sulfur introduced over a period of 1-24 hours from an initial concentration of between 100-1000 ppm by volume to a concentration of 0.1-50 ppm by volume, and subsequently continuing sulfur introduction at a concentration of 0.1-50 ppm by volume if $\Delta T$ remains above the predetermined sulfur shutoff threshold. The concentration reduction may be performed in step-wise increments.

The process may additionally include reintroducing sulfur upon $\Delta T$ increasing to or above a predetermined sulfur reintroduction threshold. The predetermined sulfur reintroduction threshold may be equal to or greater than the predetermined sulfur shutoff threshold.

An object of the invention is to reduce the amount of time after catalyst start-up before operating at optimal conditions without substantially negatively affecting catalyst performance in a transalkylation reaction. It is another object of the invention to reduce ring loss while not substantially affecting xylene yield during transalkylation.

These and other objects, features, and advantages will become apparent as reference is made to the following detailed description, preferred embodiments, examples, and appended claims.

BRIEF DESCRIPTION OF THE DRAWINGS

The FIGURE shows a not-to-scale profile of sulfur introduction verse time-on-stream for the reactor according to an embodiment of the invention.

DETAILED DESCRIPTION

According to the invention, xylene is produced by transalkylation of two or more hydrocarbon feedstocks. The process comprises:

(a) introducing sulfur into a reactor containing a catalyst system prior to first introduction of hydrocarbon feedstock into the reactor;

(b) introducing hydrocarbon feedstock into the reactor upon the concentration of sulfur downstream of the catalyst system meeting a predetermined sulfur breakthrough concentration;

(c) continuing sulfur introduction for 1-24 hours after first introducing hydrocarbon feedstock into the reactor;

(d) reducing the concentration of sulfur introduced upon $\Delta T$ decreasing to or below a predetermined sulfur reduction threshold, wherein $\Delta T$ is the difference between a temperature in the reactor upstream of the catalyst system and a temperature in the reactor downstream of the catalyst system; and (e) discontinuing sulfur introduction upon $\Delta T$ decreasing to or below a predetermined sulfur shutoff threshold, wherein the predetermined sulfur shutoff threshold is less than the predetermined sulfur reduction threshold.

Feedstocks

In one embodiment of the invention, two hydrocarbon feedstocks are used: a $C_{9+}$ aromatic hydrocarbon feedstock and a $C_6$-$C_7$ aromatic hydrocarbon feedstock.

As used herein the term "$C_n$+", wherein n is a positive integer, means a compound or group containing at least n carbon atoms. In addition, the term "$C_n$+ aromatic hydrocarbon feedstock", wherein n is a positive integer, means that a feedstock comprising greater than 50 wt % of aromatic hydrocarbons having at least n number of carbon atom(s) per molecule.

Thus, the heavy aromatic feedstock used in the present process comprises greater than 50 wt %, conveniently at least 80 wt %, typically at least 90 wt %, of one or more aromatic compounds containing at least 9 carbon atoms. Specific $C_9$+ aromatic compounds found in a typical feed include mesitylene (1,3,5-trimethylbenzene), durene (1,2,4,5-tetramethylbenzene), hemimellitene (1,2,4-trimethylbenzene), pseudocumene (1,2,4-trimethylbenzene), ethyltoluenes, ethylxylenes, propyl-substituted benzenes, butyl-substituted benzenes, and dimethylethylbenzenes. Suitable sources of the $C_9$+ aromatics are any $C_9$+ fraction from any refinery process that is rich in aromatics, such as, but not limited to, catalytic reformate, FCC naphtha or TCC naphtha.

The feed to the process also includes benzene and/or toluene ($C_6$-$C_7$) feedstock, typically toluene. The feed may also include unreacted toluene and $C_9$+ aromatic feedstock that is recycled after separation of the xylene product from the effluent of the transalkylation reaction. Typically, the $C_6$ and/or $C_7$ aromatic hydrocarbon constitutes up to 90 wt %, such as from 10 to 70 wt % of the entire feed, alternatively up to 100 wt %, whereas the $C_9$+ aromatics component constitutes at least 10 wt %, such as from 30 to 85 wt %, alternatively up to 100 wt % of the entire feed to the transalkylation reaction.

The feedstock may be characterized by the molar ratio of methyl groups to single aromatic rings. In some embodiments, the combined feedstock (the combination of the $C_9$+ and the $C_6$-$C_7$ aromatic feedstocks) has a molar ratio of methyl groups to single aromatic rings in the range of from 0.5 to 4, such as from 1 to 2.5, for example from 1.5 to 2.25.

Catalyst System

The catalyst system may comprise multiple, preferably two or three catalyst beds in the reactor. Each catalyst bed may accommodate a different catalyst. For example, in a two bed configuration, a first catalyst may reside in the upstream bed and second catalyst may reside in the downstream bed. Each catalyst may comprise a molecular sieve, either the same or different. At least one of the catalysts, and potentially each of the catalysts may comprise a hydrogenation component. Useful molecular sieves catalyst components include zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM-49, MCM-56, EMM-10, EMM-10-P, ZSM-20, PSH-3, SSZ-25, ZSM-5, ZSM-11, ZSM-22, ZSM-23, ZSM-35, ZSM-48, ZSM-57 and ZSM-58. Useful hydrogenation catalyst components may include tungsten, vanadium, molybdenum, rhenium, chromium, manganese, tin, a metal selected from Groups 6-10 of the Periodic Table of the Elements, or mixtures thereof. Additional examples of useful metals are iron, ruthenium, osmium, nickel, cobalt, rhodium, iridium, and noble metals such as platinum or palladium.

As an example, the first catalyst may comprise a molecular sieve from the group consisting of MCM-22, PSH-3, SSZ-25, ZSM-12, and zeolite beta, and a hydrogenation component comprising a metal selected from the group of platinum, palladium, or rhenium, or combinations thereof, while the second catalyst comprises a molecular sieve of ZSM-5, as disclosed in U.S. Pat. No. 5,942,651. In a specific example, the first catalyst comprises ZSM-12 and platinum while the second catalyst comprises ZSM-5. In an alternative example, the first catalyst comprises ZSM-12 and a hydrogenation component, the hydrogenation component comprising platinum and tin while the second catalyst comprises ZSM-5.

As another example, the first catalyst may comprise a molecular sieve from the group consisting of at least one of ZSM-5, ZSM-11, ZSM-22, ZSM-23, ZSM-35, ZSM-48, ZSM-57 and ZSM-58 and a hydrogenation component comprising one metal selected from the group of platinum, palladium, or rhenium, or combinations thereof; and the second catalyst comprises a molecular sieve from the group consisting of at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM-49, MCM-56, EMM-10, EMM 10-P and ZSM-20, and a hydrogenation component comprising one metal selected from the group of platinum, palladium, or rhenium, or combinations thereof. In a further example in which three catalyst beds are utilized; the previous example may additionally include a third catalyst comprising a molecular sieve of ZSM-5. In yet a further example in which three catalyst beds are utilized; the previous three catalyst bed example's first and/or second catalyst may have a hydrogenation component comprising platinum and tin.

Any or all of the catalysts may also contain a binder or matrix material in an amount ranging from 5 to 95 wt %, and typically from 10 to 60 wt %. Preferably the binder or matrix material is resistant to the temperatures and other conditions employed in the transalkylation process. Such materials include active and inactive materials and synthetic or naturally occurring zeolites, as well as inorganic materials such as clays, silica and/or metal oxides such as alumina.

Additional details of the transalkylation catalyst system may be found in the patents and patent applications described in U.S. Pat. Nos. 5,942,651 and 7,663,010, and also U.S. Pat. Nos. 6,864,203; 6,893,624; 7,485,765; 7,439,204; 7,553,791; and 5,763,720.

Transalkylation Apparatus and Process

The catalyst beds may be located in separate reactors but are conveniently located in a single reactor, typically separated from one another by spacers or by inert materials, such as, alumina balls, alumina extrudate, or sand. Generally, the catalysts are not mixed and the hydrocarbon feedstocks and hydrogen are arranged to contact the first catalyst bed prior to contacting the second catalyst bed and to contact the second catalyst bed prior to contacting the third catalyst bed, and so forth for subsequent catalyst beds.

In one example of operation, the first catalyst bed is maintained under conditions effective to dealkylate aromatic hydrocarbons containing $C_2+$ alkyl groups in the heavy aromatic feedstock and to saturate the resulting $C_2+$ olefins and the second catalyst bed is maintained under conditions effective to transalkylate $C_9+$ aromatic hydrocarbons with said at least one $C_6$-$C_7$ aromatic hydrocarbon. Obviously, where the first, second and optional additional catalyst beds are located in a single reactor, the operating conditions in each bed are substantially the same. Suitable conditions for operation of the both catalyst beds comprise a temperature in the range of about 100 to about 800° C., preferably about 300 to about 500° C., a pressure in the range of about 790 to about 7000 kPa-a, preferably about 2170 to 3000 kPa-a, a $H_2$:HC molar ratio in the range of about 0.01 to about 20, preferably about 1 to about 10, and a WHSV in the range of about 0.01 to about 100 $hr^{-1}$, preferably about 1 to about 20 $hr^{-1}$.

The transalkylation process is exothermic, particularly during the initial period of a catalyst cycle where the catalyst may be overactive. The exotherm of the reaction is an indicator of catalyst activity. The exotherm can be measured by taking the difference between the temperature in the reactor downstream of the catalyst system, or at the reactor outlet, and the temperature in the reactor upstream of the catalyst system, or at the reactor inlet. This value is also referred to as $\Delta T$ herein. Temperature in the reactor may be measured as is known in the art.

The inventive transalkylation process involves the introduction of sulfur based on exotherm thresholds. This is particularly beneficial because each transalkylation cycle may differ from other cycles based on catalyst batches, feedstock quality and availability, and other reaction conditions which may vary substantially from cycle to cycle. The current invention thus provides a controlled passivation process that is readily repeatable yet specifically tailored to each individual cycle's combination of catalyst batch, feedstock and reactor conditions. Moreover, the inventive process has proven to result in quicker de-edging periods than previously known sulfiding processes.

An embodiment of the process may be described in relation to the FIGURE. The FIGURE provides a not-to-scale plot of concentration of sulfur introduced verse time-on-stream for a transalkylation process according to the present invention. Sulfur introduction may comprise flowing hydrogen which contains $H_2S$ gas at elevated temperature such as from above room temperature to about 500° C., preferably 100° C. to 450° C. Alternatively, liquid DMDS (dimethyl disulfide) may be injected into the reactor which upon entering the reactor may decompose to $H_2S$ and methane. Sulfur introduction is preferably performed upstream of the catalyst system.

At time A, sulfur may be added to the reactor, which contains the catalyst system in situ. At this time, hydrocarbon feedstock has not yet been introduced. This period of sulfur introduction may be considered "pre-sulfiding" as this takes place before initial oil-in. Pre-sulfiding may be performed at sulfur concentrations of between 100-1000 ppm by volume, alternatively between 400-600 ppm by volume, and may be performed until sulfur "breakthrough" occurs. Sulfur breakthrough occurs when a predetermined amount of sulfur is measured downstream from the catalyst system, advantageously at or in proximity to the reactor outlet. Specifically, this amount, which may be referred to as a predetermined sulfur breakthrough concentration, may be preset based on the specific catalyst system. In an embodiment, the predetermined sulfur breakthrough concentration may be between 1-200 ppm by volume. This concentration indicates that a desired amount of sulfur has contacted all of the catalyst system. In practice, as pre-sulfiding is performed, sulfur (in the form of hydrogen sulfide) concentration may be periodically or continuously measured downstream of the catalyst system, or at or in proximity to the reactor outlet. Alternatively, sulfur breakthrough may be indicated by the observance or measurement of any amount of sulfur downstream of the catalyst system after sulfur introduction upstream of the catalyst system. For example, the presence of sulfur downstream of the catalyst system may be observed by drager tube as is known in the art or alternatively by contacting a sample of the reactor effluent with lead acetate and observing for change in color. When the sulfur concentration downstream of the catalyst system meets or exceeds the predetermined sulfur breakthrough concentration, the period of pre-sulfiding may end at time B as shown on the FIGURE.

Hydrocarbon feedstocks may be introduced at time B to the reactor upon the sulfur concentration at the reactor outlet meeting the predetermined sulfur breakthrough concentration. As used herein, the term "upon" indicates causality and is not intended to necessarily have a temporal connotation. In other words, the hydrocarbon feedstock is introduced at time B, which may be any time, simultaneous, before, or after the time that sulfur concentration downstream of the catalyst system meets or exceeds the predetermined sulfur breakthrough concentration, as long as such introduction is based on the sulfur breakthrough concentration trigger. For example, feedstock introduction at time B may occur shortly after a measured sulfur concentration at the reactor outlet meets the predetermined sulfur breakthrough concentration. The period of sulfiding starting at time B and ending at time C may be considered the initial co-sulfiding period, and may continue for 1-24 hours after first introducing hydrocarbon feedstock into the reactor. Sulfur may be introduced during the initial co-sulfiding period at sulfur concentrations of between 100-1000 ppm by volume, alternatively by 400-600 ppm by volume and may be the same concentration as that used in the pre-sulfiding period.

The reaction starts at time B, after which an exotherm develops in the reactor. The exotherm, or $\Delta T$, may be determined by periodic or continuous measurement of temperature in the reactor upstream from the catalyst system, or alternatively at the reactor inlet, and in the reactor downstream from the catalyst system, or alternatively at the reactor outlet, and calculating the difference. This exotherm may initially be up to 70-100° C. but generally subsides over time due to sulfiding and coking of the catalyst. Upon $\Delta T$ decreasing to or below a predetermined sulfur reduction threshold, the concentration of sulfur introduced may be reduced. The predetermined sulfur reduction threshold may be between 25-75° C.

The sulfur concentration may be reduced over a period of time, for example 1-24 hours, gradually or in step-wise increments. Reduction may be performed by set amounts at set time intervals. For example, sulfur concentration reduction may be performed in 4 steps of 25% reduction at each step, which occur every 2.5 hours. A step-wise reduction of this nature is shown in the FIGURE. Alternatively, any number of equal (e.g., 5 reductions of roughly 20%) or non-equal reductions may be performed at equal or non-equal periods of time.

Reduction may alternatively be performed based on correlation to decreasing $\Delta T$. For example, the predetermined sulfur reduction threshold may be set at 50° C. Upon $\Delta T$ meeting the threshold, the sulfur concentration may be reduced by 25% at time C. Over time, $\Delta T$ should generally decrease. Upon decreasing to or below an intermediate reduction threshold, the sulfur concentration may be reduced by a further 25%. This process of reduction may be continued until the sulfur concentration reduction period ends at time D.

When sulfur concentration reduction is performed based on a set time interval, time D may occur at such a set time, for example, sulfur concentration reduction may be accomplished in 4 steps over a set period of 10 hours, and thus, time D occurs at 10 hours after time C. If at time D, $\Delta T$ has decreased to or below a predetermined sulfur shutoff threshold, sulfur introduction may be discontinued. If $\Delta T$ remains above the predetermined sulfur shutoff threshold at time D, then sulfur introduction may be continued at a low concentration, for example between 0.1-50 ppm by volume. In the embodiment in which sulfur concentration is reduced step-wise, and $\Delta T$ remains above the predetermined sulfur shutoff threshold at time D, then the last reduction step would be made to a concentration of 0.1-50 ppm by volume instead of 0 ppm, as shown in the FIGURE. The predetermined sulfur shutoff threshold may be between 5-25° C.

When sulfur concentration reduction is performed based on correlation to decreasing $\Delta T$, then time D may occur when $\Delta T$ decreases to or below the predetermined sulfur shutoff threshold, in which case sulfur introduction may be discontinued, or alternatively when $\Delta T$ decreases to or below a predetermined sulfur maintenance threshold, in which case sulfur introduction may be continued at a low concentration, for example between 0.1-50 ppm by volume. The predetermined sulfur maintenance threshold may be between 5-25° C., but is in any case above the predetermined sulfur shutoff threshold.

The process may also include continuing sulfur introduction at a low concentration, for example 0.1-50 ppm by volume, if $\Delta T$ remains above the predetermined sulfur shutoff threshold after sulfur concentration reduction. In this embodiment, sulfur introduction is continued for a period of time until $\Delta T$ decreases below the predetermined sulfur shutoff threshold at time E as shown in the FIGURE. At time E, sulfur introduction may be discontinued. This period of continued sulfur introduction between times D and E may be as long as multiple weeks (note that the FIGURE is not to scale in this regard) and may coincide with the de-edging or line-out period for the cycle in which the transalkylation reaction is performed at suboptimal conditions in order to manage and/or controllably lower a fresh catalyst's overly-active hydrogenation activity. During this de-edging period, the reactor may be operated at a hydrogen partial pressure that is substantially lower than the optimal design hydrogen partial pressure for transalkylation with the reactor. Sulfiding according to the current invention additionally permits the transalkylation reaction to be performed at suboptimal feed rate/weight hourly space velocity (WHSV) while keeping $\Delta T$ in a desirable range, which may correlate to desirable levels of dealkylation, feed olefin saturation, ring loss, and/or ring cracking.

After sulfur introduction has been discontinued, either at time D or E or otherwise, sulfur may be reintroduced upon $\Delta T$ increasing to or above a predetermined sulfur reintroduction threshold (shown at time F on the FIGURE). The predetermined sulfur reintroduction threshold may be equal to or greater than the predetermined sulfur shutoff threshold. The predetermined sulfur reintroduction threshold may be between 10-30° C.

Minimizing Sulfur Addition

Due to the risks of sulfiding, i.e., possible permanent damage to the catalyst metal function, potential exposure to $H_2S$, and environmental concerns, it is desirable to minimize the amount of sulfur added to the transalkylation process during the pre-sulfiding and co-sulfiding steps. Manipulating the composition of the feedstock during initial oil-in and subsequent hours of operation may allow for such reduction of sulfur necessary to temper metal function.

The addition of benzene and/or xylenes to the feedstock during the initial oil-in and for a relatively short time thereafter, which may be up to a week, preferably 3-4 days, can reduce the amount of sulfur necessary to effectively pre-sulfide and co-sulfide the catalyst. Benzene and xylenes are the principle products of the transalkylation reactions involving toluene and $C_{9+}$ aromatics. By adding xylenes to the reactor feed, the reaction equilibrium is shifted in reverse, limiting the conversion. Xylenes are also less susceptible to ring loss reactions than benzene or toluene, and do not undergo exothermic dealkylation reactions like alkyl-substituted $C_{9+}$ aromatics. These impacts on the reaction chemistry result in lower hydrogen consumption, decreased gas make, and reduced reactor temperature increase. Therefore, the amount of sulfur added during the co-sulfiding step can be reduced.

Another benefit of adding benzene and/or xylenes to the feedstock is to increase the overall feed rate, or WHSV, to the reactor. The higher WHSV is the result of two factors: 1) the presence of the xylenes provides more feed to reactor, and 2) the lower toluene/$C_{9+}$ aromatics conversion provides higher recycle rates, thus increasing the feed to the reactor. The increased WHSV results in reduced residence time of feedstock in the reactor, which will lower the conversion of the reactants, thus not creating as large of an exotherm. Lastly, the higher WHSV provides additional material to act as a heat sink, absorbing the heat of reaction and further limiting temperature rise.

The benzene and/or xylenes may be added directly to the transalkylation feedstock or upstream fractionation processes may be adjusted to allow benzene and/or xylenes that would ordinarily be fractionated and sent elsewhere in the process to be sent to transalkylation with the toluene and $C_{9+}$ aromatics. For instance, with respect to benzene, an upstream benzene recovery column, which typically recovers substantially all of the benzene as an overhead stream and produces a bottoms stream containing toluene, may be adjusted to increase the amount of benzene rejected to the bottoms stream to increase the amount of benzene in the toluene stream. Likewise, with respect to xylenes, an upstream xylenes fractionation column, which typically recovers xylenes as an overhead stream and produces a bottoms stream containing $C_{9+}$ aromatics, may be adjusted to increase the amount of xylenes rejected to the bottoms stream to increase the amount of xylenes in the $C_{9+}$ aromatics stream.

Example 1

Two reactors were loaded with the multi-stage transalkylation catalyst system as described in U.S. Pat. No. 7,663,010. Reactor #1 was started up under the conventional practice of pre-sulfiding, introduction of a feedstock comprising mainly toluene and $C_{9+}$ aromatics, and co-sulfiding. Reactor #2 was started up under similar conditions, except that the feedstock also included xylenes. Table 1 below summarizes the operating conditions, feed composition, and the amount of sulfur added for the pre-sulfiding and co-sulfiding steps. The sulfur addition is reported in units of molar equivalents of the catalyst metal content.

TABLE 1

| Conditions at Oil-in + 1 day | Reactor #1 | Reactor #2 |
|---|---|---|
| Toluene content of Feed (wt %) | 55-60 | 55-60 |
| $C_{9+}$ Aromatics content of Feed (wt %) | 40-45 | 25-30 |
| Xylenes content of Feed (wt %) | <1 | 15-20 |
| Pressure (MPa-g) | 2-2.25 | 2-2.25 |
| WHSV ($hr^{-1}$) | 2.5-2.75 | 2.25-2.5 |
| Reactor Inlet Temperature (° C.) | 350 | 350 |
| Temperature rise across reactor (° C.) | 58 | 56 |
| Total Sulfur Added, equivalents | 24.6 | 15.0 |

Table 1 shows that as a result of including xylenes in the feedstock, the amount of sulfur addition required for the pre-sulfiding and co-sulfiding steps decreased by about 40%. Despite having a lower feed rate to remove reaction heat, the temperature rise for Reactor #2 was essentially the same as that of Reactor #1. The presence of xylenes in the liquid feed provided essentially the same operability of the reactor with the long-term benefit of reduced exposure of the catalyst to sulfur. The Reactor #2 feed xylene content was returned to normal after approximately 3.5 days-on-stream without incident.

Trade names used herein are indicated by a™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention.

What is claimed is:

1. A process for producing xylene by transalkylation of two or more hydrocarbon feedstocks, the process comprising:
   (a) introducing sulfur into a reactor containing a catalyst system prior to first introduction of the two or more hydrocarbon feedstocks into the reactor in an initial sulfiding period;
   (b) measuring a concentration of sulfur downstream of the catalyst system and continuing introducing sulfur into the reaction until the concentration of sulfur downstream of the catalyst system has met a predetermined sulfur breakthrough concentration;
   (c) introducing the two or more hydrocarbon feedstocks into the reactor after the sulfur concentration downstream of the catalyst system meets the predetermined sulfur breakthrough concentration;
   (d) transalkylating at least some of the two or more hydrocarbon feedstocks in the presence of the catalyst system to produce xylene;
   (e) continuing sulfur introduction in a de-edging period for 1-24 hours after introducing the two or more hydrocarbon feedstocks into the reactor in (c);
   (f) measuring the temperature of the reactor upstream of the catalyst system and the temperature of the reactor downstream of the catalyst system to calculate ΔT, wherein ΔT is the difference between the temperature in the reactor upstream of the catalyst system and the temperature in the reactor downstream of the catalyst system;

(g) reducing the concentration of sulfur introduced into the reactor when ΔT is less than or equal to a predetermined sulfur reduction threshold; and (h) discontinuing sulfur introduction when ΔT is less than or equal to a predetermined sulfur shutoff threshold, wherein the sulfur shutoff threshold is less than the sulfur reduction threshold.

2. The process of claim 1 wherein the sulfur concentration reduction of step (g) is performed over a period of 1-24 hours to a concentration of 0.1-50 ppm by volume, and sulfur introduction is continued at a concentration of 0.1-50 ppm by volume if ΔT remains above the sulfur shutoff threshold.

3. The process of claim 1 further comprising: (i) measuring ΔT and reintroducing sulfur upon ΔT increasing to or above a predetermined sulfur reintroduction threshold.

4. The process of claim 3 wherein the predetermined sulfur reintroduction threshold is equal to or greater than the predetermined sulfur shutoff threshold.

5. The process of claim 4 wherein the predetermined sulfur reintroduction threshold is between 10° C. and 30° C.

6. The process of claim 1 wherein the sulfur concentration is reduced to a concentration of 1-5 ppm by volume, and continuing sulfur introduction at a concentration of 1-5 ppm by volume if ΔT remains above the predetermined sulfur shutoff threshold.

7. The process of claim 1 wherein the sulfur concentration reduction of step (g) is performed in step-wise increments.

8. The process of claim 1 wherein sulfur is introduced into the reactor during steps (a)-(c) at a concentration of 100-1000 ppm by volume.

9. The process of claim 1 wherein the predetermined sulfur breakthrough concentration is between 1-200 ppm by volume.

10. The process of claim 1 wherein the predetermined sulfur reduction threshold is between 25° C. and 75° C.

11. The process of claim 1 wherein the predetermined sulfur shutoff threshold is between 5° C. and 25° C.

12. The process of claim 1 wherein the sulfur is introduced in the form of dimethyl disulfide.

13. The process of claim 1 wherein the sulfur is introduced in a mixture of hydrogen sulfide and hydrogen gas.

14. The process of claim 1 wherein the catalyst system comprises at least a first catalyst residing in an first catalyst bed and second catalyst residing in a second catalyst bed, wherein the second catalyst bed is downstream of the first catalyst bed, and wherein the first catalyst comprises a molecular sieve and a hydrogenation component, and the second catalyst comprises a molecular sieve.

15. The process of claim 14 wherein the catalyst system further comprises a third catalyst residing in a third catalyst bed, wherein the third catalyst bed is downstream of the second catalyst bed, and wherein the second catalyst additionally comprises a hydrogenation component, and the third catalyst comprises a molecular sieve.

16. The process of claim 15 wherein each hydrogenation component comprises platinum.

17. The process of claim 16 wherein each hydrogenation component further comprises tin.

18. A process for sulfiding a transalkylation catalyst comprising the steps of:

(a) providing a reactor containing a catalyst system for producing xylene by transalkylation of two or more hydrocarbon feedstocks;

(b) introducing sulfur into the reactor upstream of the catalyst in an initial sulfiding period;

(c) measuring a concentration of sulfur downstream of the catalyst system and continuing introducing sulfur into the reaction until the concentration of sulfur downstream of the catalyst system has met a predetermined sulfur breakthrough concentration;

(d) introducing the two or more hydrocarbon feedstocks into the reactor after the concentration of sulfur downstream of the catalyst system meets the predetermined sulfur breakthrough concentration;

(e) continuing sulfur introduction for 1-24 hours after first introducing the two or more hydrocarbon feedstocks into the reactor in a de-edging period;

(f) measuring the temperature of the reactor upstream of the catalyst system and the temperature of the reactor downstream of the catalyst system to calculate ΔT, wherein ΔT is the difference between the temperature in the reactor upstream of the catalyst system and the temperature in the reactor downstream of the catalyst system;

(g) reducing the concentration of sulfur introduced when ΔT is less than or equal to a predetermined sulfur reduction threshold; and (h) discontinuing sulfur introduction when ΔT is less than or equal to a predetermined sulfur shutoff threshold, wherein the predetermined sulfur shutoff threshold is less than the predetermined sulfur reduction threshold.

19. The process of claim 18 wherein the predetermined sulfur breakthrough concentration is between 1-200 ppm by volume.

20. The process of claim 18 wherein the predetermined sulfur reduction threshold is between 25° C. and 75° C.

21. The process of claim 18 wherein the predetermined sulfur shutoff threshold is between 5° C. and 25° C.

22. The process of claim 18 wherein the sulfur concentration reduction of step (g) is performed over a period of 1-24 hours to a concentration of 0.1-50 ppm by volume, and sulfur introduction is continued at a concentration of 0.1-50 ppm by volume if ΔT remains above the sulfur shutoff threshold.

23. The process of claim 22 wherein the sulfur concentration is reduced to a concentration of 1-5 ppm by volume, and comprises continuing sulfur introduction at a concentration of 1-5 ppm by volume if ΔT remains above the predetermined sulfur shutoff threshold.

24. The process of claim 18 wherein the sulfur concentration reduction of step (g) is performed in step-wise increments.

25. The process of claim 1 wherein the hydrocarbon feedstocks comprise benzene and/or xylenes.

* * * * *